US006403032B1

United States Patent
Abercrombie et al.

(10) Patent No.: US 6,403,032 B1
(45) Date of Patent: Jun. 11, 2002

(54) ASSEMBLY FOR DISPENSING SANITARY AGENTS INTO DRAINS

(75) Inventors: James Carman Abercrombie; Scott John Abercrombie, both of St. Mary's (CA); Curtis Walter Thomas, Kansas City, MO (US)

(73) Assignee: West Agro, Inc., Kansas City, MO (US)

( * ) Notice: Subject to any disclaimer, the term of this patent is extended or adjusted under 35 U.S.C. 154(b) by 0 days.

(21) Appl. No.: 09/901,944

(22) Filed: Jul. 9, 2001

(51) Int. Cl.[7] ............................. A01N 0/00; E03D 9/02
(52) U.S. Cl. ..................... 422/28; 422/264; 422/266; 422/276; 4/222
(58) Field of Search ..................... 422/28, 276; 4/222

(56) References Cited

U.S. PATENT DOCUMENTS

| | | | |
|---|---|---|---|
| 3,597,772 A | * | 8/1971 | Leavitt et al. ................. 4/222 |
| 4,911,859 A | | 3/1990 | Bunczk et al. |
| 5,019,346 A | * | 5/1991 | Richter et al. ................. 422/28 |
| 5,043,090 A | | 8/1991 | Camp et al. |
| 5,043,091 A | | 8/1991 | Joshi et al. |

* cited by examiner

Primary Examiner—Robert J. Warden, Sr.
Assistant Examiner—Sean E. Conley
(74) Attorney, Agent, or Firm—Hovey Williams LLP

(57) ABSTRACT

In assembly for dispensing agents into drains and the like, includes a retaining member having a perforate wall structure substantially surrounding and enclosing a quantity of a sanitizing agent therein. The retaining member is preferably flexible and tubular, and may be formed into a donut-shaped configuration. The retaining member may be provided of a mesh material. The mesh initially holds the sanitizing agent, provided as a powder or in granular form therein. Upon wetting of the sanitizing agent, it may assume a gel-like consistency and erode to dispense the sanitizing agent into the liquid passing through the retaining member. A mount may be employed to both hold the retaining member in a proper position and configuration, and to secure edges of the retaining member in a closed position.

10 Claims, 2 Drawing Sheets

ASSEMBLY FOR DISPENSING SANITARY AGENTS INTO DRAINS

BACKGROUND OF THE INVENTION

1. Field of the Invention

The present invention relates to drain sanitizing devices. More particularly the present invention concerns an iodophor-containing drain sanitizing ring assembly which conveniently provides improved cleaning and prolonged sanitizing in drains.

2. Description of the Prior Art

In an effort to combat microbiological activity in drain runoff areas many food processing facilities, and other facilities where potentially contaminated water flow is a problem, use drain sanitizing devices.

Water born diseases often caused by pathogenic microorganisms can be spread by microbiological activity in drain runoff areas in food processing environments. The need to sanitize these areas for worker and consumer health reasons has shown a need for new sanitation devices that combat these micro-organisms. Regulatory agency awareness as well as public awareness of water born diseases has increased dramatically due to the reoccurrence of epidemics.

U.S. Pat. No. 5,019,346 to Richter, et al., issued May 28, 1991, herein incorporated by reference, discloses a drain treatment product having a cavity defined by three walls. The cavity is used as a mold for and contains a sanitizing agent. In use, the outside wall and a portion of the bottom wall are removed and discarded, exposing the sanitizing agent. The drain treatment product of the '346 patent thus uses a sold, water impermeable wall mesh material to retain the sanitizing agent before and during use. Thus the product of the '346 patent acts in conjunction with the receiving drain structure whereby any remaining wall portions can trap water. While the '346 patent discloses that it is permissible to completely remove the walls, the result would fully expose the sanitizing agent to rapid and possibly undesired excessive erosion. If the sanitizing agent is fully exposed, there would be nothing to stop large portions of the agent from washing down the drain, thereby reducing the amount of sanitizing agent located adjacent to the drain opening.

Accordingly, there is a need for an improved drain sanitizing ring assembly which provides improved features not found in the prior art.

SUMMARY OF THE INVENTION

The drain sanitizing assembly of the present invention overcomes the above-identified disadvantages and provides a distinct advance in the art of drain sanitizing ring assemblies. More particularly the present invention provides an iodophor-containing drain sanitizing ring assembly, which conveniently provides improved cleaning and prolonged sanitizing in drains.

The dispensing assembly comprises a quantity of a sanitizing agent and a fluid-permeable retaining member which surrounds and holds the sanitizing agent therein, preferably provided as a flexible tube of a mesh material for containing the sanitizing agent therein. In preferred forms, the present invention includes a mount whereby the flexible retaining member, preferably provided as a donut-shaped tube, may more readily be properly positioned in the drain and which helps to retain the tube in a desired configuration. In a particularly preferred embodiment, the mount is cylindrical in shape having having a top circular edge and a bottom circular edge, and helps to hold the tube in a generally toroidal configuration and secure the edges of the tube. Most preferably the mount includes a first rigid ring section of slightly smaller outside diameter than the inside diameter of the retaining member, and a second rigid ring section, of slightly smaller outside diameter than the inside diameter of the first ring section, thereby providing frictional engagement between the mount and the tube-shaped retaining member for holding the edges of the tube therebetween.

The sanitizing agent as used herein may be any one of a number of solid or semi-solid compounds or mixtures which provide bacteriocidal efficacy. Chemicals which may be used as sanitizing agents include aldehydes, iodophors, phenolic, surfactants including anionic and cationic surfactants, and inorganic and organic chlorine releasing agents. One particularly used compound as a sanitizing agent includes 61.3% Calcium Sulphate; an iodophor; Guar Gum; Peg Disterate; Polyox Coagulant; Sodium Silicate; and Carbopol. Preferably, the sanitizing agent is provided in granular or powdered form which may be arranged into the form of a ring. The size of the ring may vary depending on the size of the drain, but by way of example may have an inside diameter of about four inches, an outside diameter of about six inches and a cross-sectional diameter of two inches.

The retaining member is provided and arranged to be permeable to water while initially retaining the sanitizing agent therein. For example, the retaining member may have a perforate wall which preferably does not absorb water. One example is a flexible mesh material which both permits liquid to flow therethrough while gradually releasing the sanitizing agent and which permits the assembly to at least partially conform and adjust to the drain.

The mount may be used to position the assembly in the drain. For example, when the assembly hereof is to be inserted into a generally circular drain opening, the mount may be provided as a substantially rigid cylinder around which the retaining member is arranged. The mount thus provides the desired spacing and prevents the retaining member from collapsing over the drain opening. The cylinder may be provided, for example, of two ring sections of synthetic resin such as polyvinyl chloride or more preferably ABS resin. An inner ring section may thereby frictionally engage an outer ring section with a portion of the retaining member secured therebetween to help close the edges of the retaining member, thereby inhibiting escape of the sanitizing agent and maintaining the position and conformation of the retaining member and the sanitizing agent therein.

In use the ring assembly is placed into a drain opening. Water flowing down the drain passes by the ring assembly and saturates the sanitizing agent, thereby wetting and controllably releasing the sanitizing agent. In the particularly preferred form of the invention, the sanitizing agent assumes a gel-like consistency when wetted, which is held within the retaining member and gradually leaches into the liquid passing through the retaining member. The released sanitizing agent then substantially sanitizes the water flowing from the drain.

These and other important features of the present invention are more fully described in the section title DETAILED DESCRIPTION OF A PREFERRED EMBODIMENT, below.

DESCRIPTION OF THE PREFERRED EMBODIMENT

Figure 1:
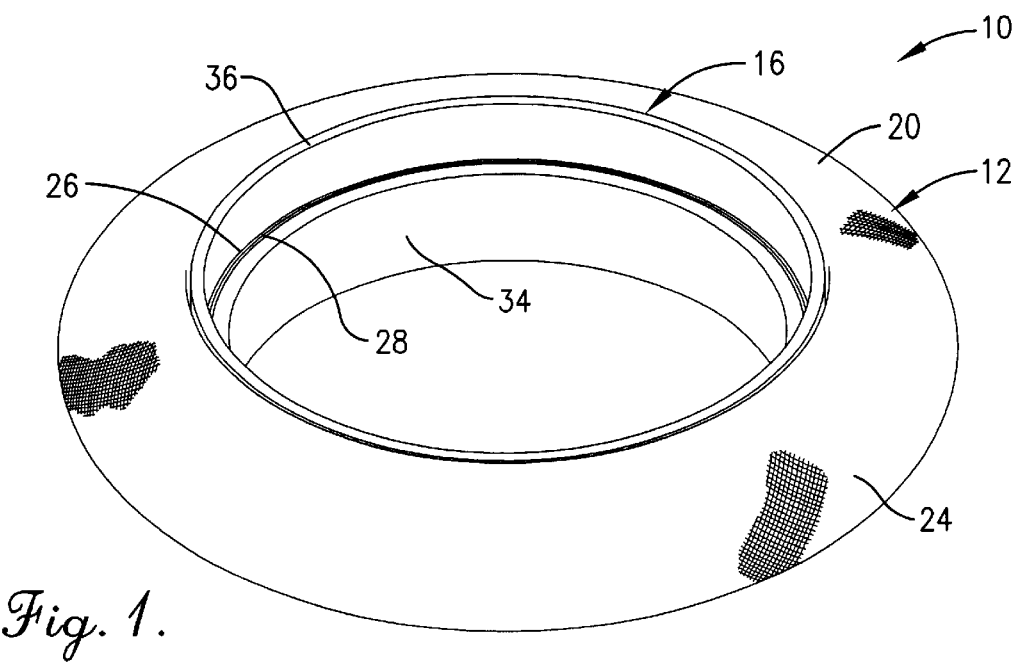
FIG. 1 is a perspective view of the assembly for dispensing sanitizing agents in accordance with the preferred embodiment of the present invention showing the retaining member in a toroidal configuration around the mount.

Referring now to the drawings, an assembly 10 for dispensing sanitary agents into drains broadly includes a retaining member 12 which is constructed to be permeable to liquids and which encloses therein a sanitizing agent 14. The retaining member 12 is preferably held and supported by a mount 16. The assembly 10 may be sized and configured for receipt into a drain 18, such as a floor drain as illustrated.

Figure 2:
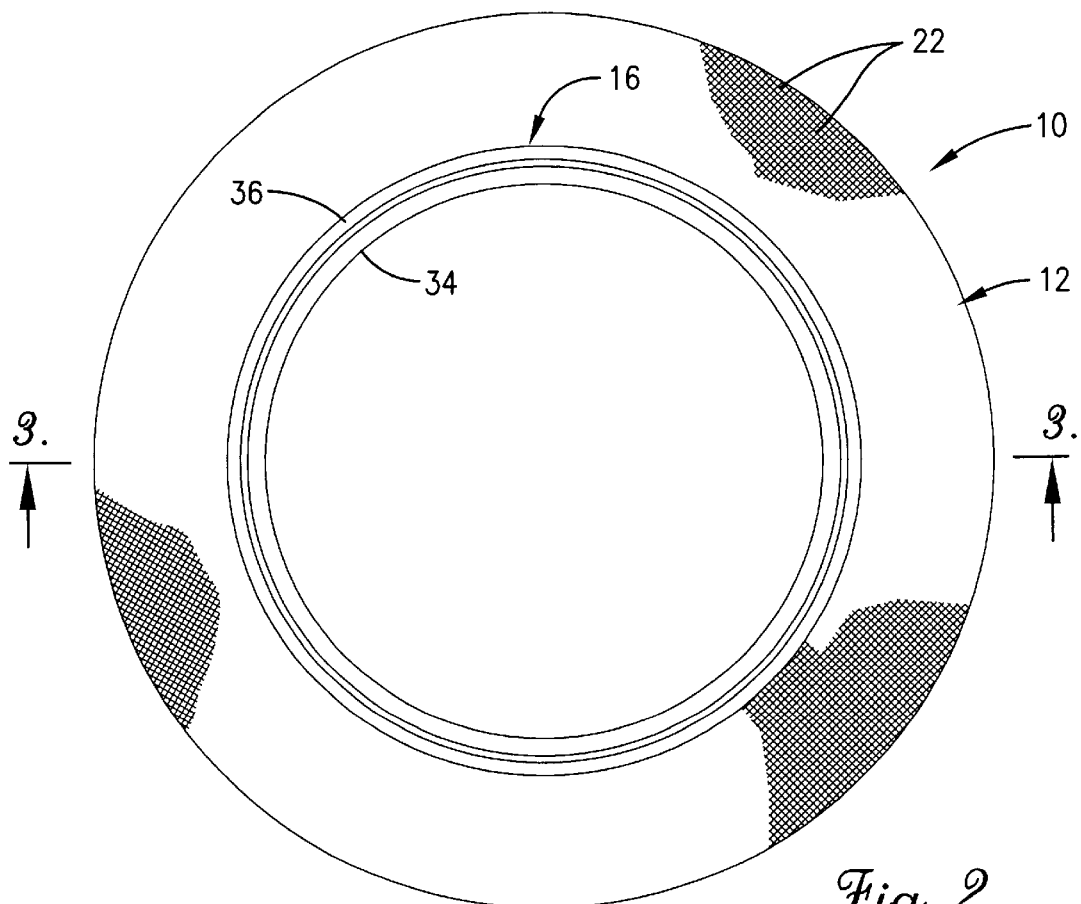
FIG. 2 is a plan view thereof, showing the frictional engagement between the inner and outer ring sections.
Figure 3:
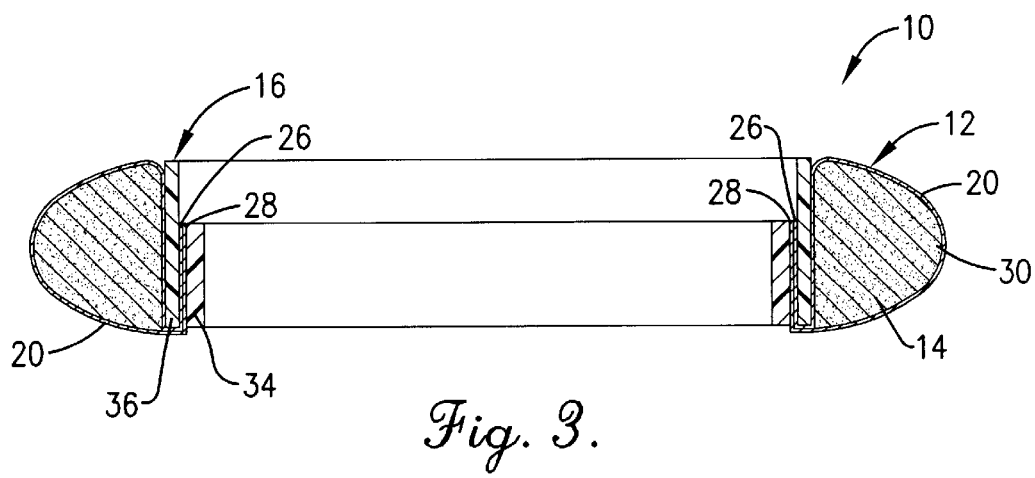
FIG. 3 is a vertical cross-sectional view thereof taken along line 3—3 of FIG. 2 to show the sanitizing agent within the retaining member.
Figure 4:
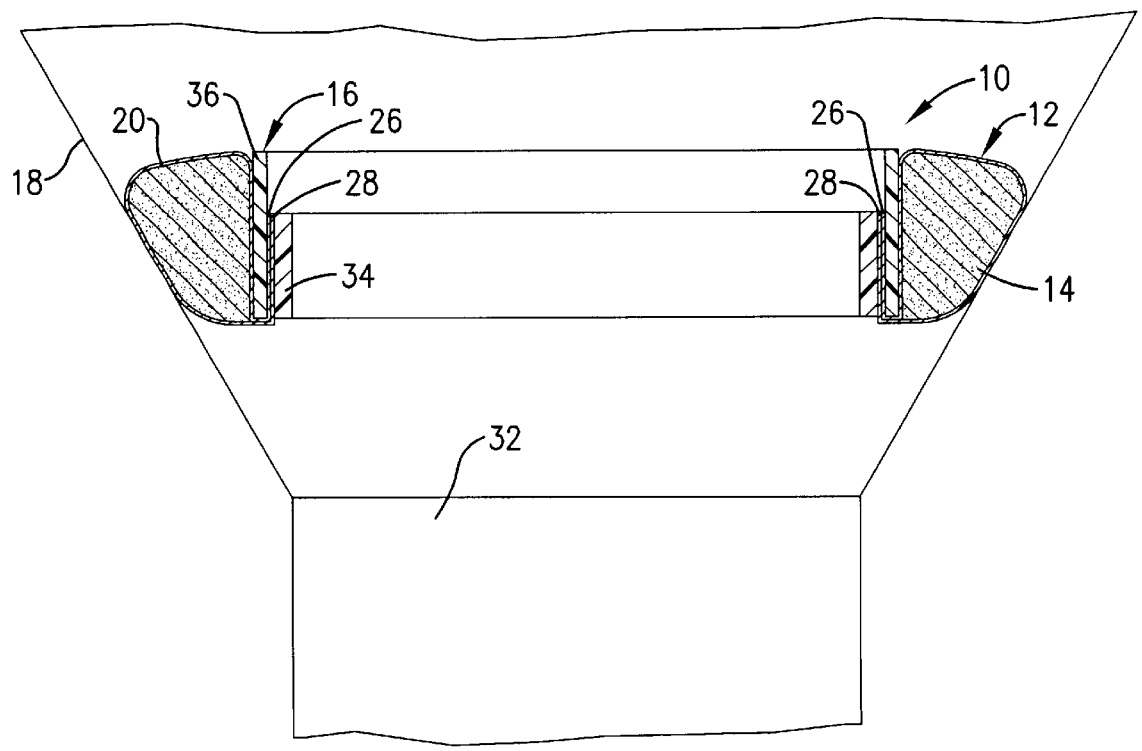
FIG. 4 is a cross-sectional view similar to FIG. 3, showing the assembly positioned within a circular drain.

In greater detail, the retaining member 12 includes a wall 20 which is configured to surround and enclosing therein the sanitizing agent 14, and is preferably provided with a plurality of small openings 22 therein. The openings may most advantageously be provided by constructing the wall 20 of a flexible mesh material 24. The mesh material 24 is substantially non-absorbent to liquids, and provided of a synthetic resin material, with the openings 22 sized sufficiently small so as to inhibit the escape of the sanitizing agent in a powder or granular form. A preferred mesh material 24 is made of polyester is a 34 filament, continuously knitted, of 135 denier and a density of 95 grams per square meter. Such a mesh has a thickness of approximately 1 mm and is non-biodegradable. While the retaining member 12 may be elongated or of other configurations corresponding to the shape of the drain 18 into which it is received, it is preferably provided to be toroidal in shape as assembled. As shown in FIGS. 1 and 2, the mesh material 24 is most preferably knitted continuously to form a circular shape, and as shown in FIGS. 3 and 4, the mesh material 24 has a first edge 26 and a second edge 28 which are folded together in substantial adjacency, thereby providing a tubular construction for receiving the sanitizing agent in the volume 30 thereby created.

The sanitizing agent 14 is received in the volume 30 and may be any one of a number of suitable sanitizing compositions having bacteriocidal efficacy, including, for example, chemical compositions including aldehydes, iodophors, phenolics, surfactants including anionic and cationic surfactants, and organic and inorganic chlorine releasing agents, such as alkyl (60% $C_{14}$, 30% $C_{16}$, 5% $C_{12}$, 5% $C_{18}$) dimethyl benzyl ammonium chlorides. A particularly useful sanitizing agent 14 hereof includes an active iodophor composition, and a quantity of calcium sulphate, guar gum, PEG disterate, polyox coagulant, sodium silicate, and a surfactant such as those sold under the trademark Carbopol. The preferred sanitizing agent 14 is granular or more preferably a powder in its initial state prior to wetting, and after wetting has a gel-like consistency such that the powder particles are no longer discrete. A particularly preferred composition for the sanitizing agent is formulated including as the iodophor Clean Front Concentrate available from West Agro, Inc. of Kansas City, Mo., as follows:

| | |
|---|---|
| calcium sulphate | 61.3% |
| sodium silicate | 1.9% |
| Clean Front Concentrate | 12.6% |
| Polyox coagulant | 2.3% |
| PEG distearate | 10.7% |
| Guar gum | 10.7% |
| Carbopol | 0.4% |

The composition of the sanitizing agent 14 as set forth above provides an iodine concentration of at least about 2.65%.

The mount 16 may be employed to position the retaining member 12 in a position which brings the sanitizing agent 14 into contact with the liquid, such as water, to be sanitized, and to retain the general shape of the retaining member 12, thus permitting the liquid to flow through the mesh without covering the opening 32 of the drain 18. Beneficially, the mount 16 also provides a closure mechanism for the edges 26 and 28. The mount 16 is of a non-absorbent, substantially rigid material such as ABS synthetic resin, although metals, ceramics, or other synthetic resins such as polyvinyl chloride may be used. For use with the circular drain 18 shown in FIG. 4, the mount 16 is provided as a first ring section 34 and a second ring section 36 interfitted in frictional engagement. The first ring section 34 has an inner diameter greater than that of the opening 32 and an outer diameter less than the inner diameter of the retaining member 12. The second ring section 36 has an inner diameter only slightly greater than the outer diameter of the first ring section 34, and an outer diameter less than the inner diameter of the retaining member 12. Thus, the first ring section 34 may fit within and frictionally engage the second ring section 36, with the edges 26 and 28 being captured between the ring sections 34 and 36 and extending circumferentially around the outer surface 38 of the first ring section and circumferentially around the inner surface 40 of the second ring section 36. When the ring sections 34 and 36 are assembled, the mount 16 is of sufficient depth to prevent sagging of the flexible retaining member 12 and provides good positioning of the assembly 10 within the drain 18.

An assembly 10 having a nominal 4 inch diameter circular mount 16 and approximately 165 grams of sanitizing agent 14 received within the preferred retaining member 12 having an outer diameter of about 6 inches was tested with the following results:

The assembly was placed in the bottom of a 4 liter beaker and de-ionized water was added to the 2 liter mark. The iodine concentration was measured at the top, middle and bottom of the water column following 5 days of immersion. The water was poured off and replaced by de-ionized water to the 2 liter mark. The iodine concentration was again measured after 4.5 hours of immersion. Thereafter, the water was again poured off and replaced to a level only sufficient to completely cover the assembly 10, a depth of about 1 and ½ inches. At the same time, a second assembly 10 was placed in a separate 4 liter beaker and covered with de-ionized water again to a level only sufficient to completely cover the assembly 10, a depth of about 1 and ½ inches. The iodine concentrations for both the first assembly and the second assembly were again measured following 24 hours of immersion, with the sample being taken from the center of the beaker midway in the depth of the water column. The first assembly revealed the iodine concentrations to be as follows:

| Time | Top | Middle | Bottom |
| --- | --- | --- | --- |
| 5 days immersion | 0.6 | 1.0 | 810 |
| +4.5 hours immersion | 13 | 14 | 36 |
| +24 hours immersion | | 107 | |
| | | (reduced water volume) | |

The second assembly revealed the iodine concentration as follows:

| Time | Middle |
| --- | --- |
| 24 hours | 66 (reduced water volume) |

The assembly of the present invention is easily assembled by simply placing the desired quantity of sanitizing agent 14 distributed around the inside of the retaining member 14 and then folding the edges 26 and 28 together to provide a donut or toroidal shape to the retaining member 14. The edges 26 and 28 are then placed against the outside surface of the first ring section 34 and then captured as the second ring section 36 is pressed over the first ring section 34. Although the ring sections 34 and 36 may be sufficiently pressed together to completely overlap, only a small amount of overlap, as shown in FIGS. 3 and 4, is sufficient to assemble the mount 16 and hold the retaining member 12 in proper position and completely enclose the sanitizing agent 14 therein.

In use, the assembly 10 is simply placed in the drain 18 so that the drain opening 32 is not occluded, the mount 16 keeping the central area above the drain opening 32 clear. As water enters the drain and contacts the sanitizing agent 14, the powder is wetted, changing the consistency of the sanitizing agent 14 to that of a gel. Water is permitted to flow through the flexible retaining member 12 and erode the sanitizing agent to release the active material into the water for bacteriocidal effect. However, the retaining member 12 substantially surrounds the wetted sanitizing agent 14 and provides protection against accelerated erosion due to water impact, as well as preventing the gel-like agent 14 from flowing out of the drain opening 32 as a mass. The useful life of the assembly 10 largely depends on the flow of water therepast. Once the sanitizing agent 14 is depleted, evidenced by the collapse of the retaining member 12, the assembly is replaced. Thus, the flexible retaining member 12 also provides a visual indicator of whether the assembly 10 is continuing to perform its sanitizing function.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the doctrine of equivalents to determine and assess the reasonably fair scope of his invention as pertains to any apparatus not materially departing from but outside the literal scope of the invention as set out in the following claims.

What is claimed is:

1. An assembly for dispensing sanitary agents into drains comprising:

a quantity of sanitizing agent which is initially in granular or powdered form when unwetted; and a retaining member defining a volume and substantially surrounding the sanitizing agent therein, said retaining member including a wall of flexible mesh fabric material having a plurality of openings sized to permit the passage of liquid therethrough and to permit gradual erosion of the sanitizing agent from the retaining member while inhibiting the passage of said sanitizing agent therefrom in an initial, unwetted condition, said granular or powdered sanitizing agent characterized by the property of becoming a gel upon wetting thereof with said fabric material conforming to the sanitizing agent during gradual release of the sanitizing agent through the fabric material.

2. An assembly as set forth in claim 1, wherein the mesh material is provided of synthetic resin which is substantially non-absorbent.

3. An assembly as set forth in claim 2, wherein the retaining member is substantially toroidal.

4. An assembly as set forth in claim 3, including a mount coupled to the retaining member.

5. An assembly as set forth in claim 4, wherein the mesh retaining member wall includes first and second edges, and wherein said mount is coupled to said first and second edges to enclose the sanitizing agent within the retaining member.

6. An assembly as set forth in claim 5, wherein the mount includes a first ring member interfitted with a second ring member to clamp the first and second edges therebetween.

7. An assembly as set forth in claim 6, wherein the mount is positioned substantially interiorly of the retaining member.

8. An assembly as set forth in claim 1, including a mount coupled to the retaining member.

9. An assembly as set forth in claim 1, wherein the sanitizing agent includes an iodophor.

10. A method for sanitizing drains comprising the steps of:

providing a drain assembly including a quantity of sanitizing agent which is initially in granular or powdered form when unwetted and a retaining member substantially surrounding the retaining member and including a wall of flexible mesh fabric material having a plurality of openings for permitting the passage of liquid therethrough while inhibiting the passage of said sanitizing agent therefrom in an initial, unwetted condition;

wetting the drain assembly with liquid to be sanitized whereupon the initially granular or powdered sanitizing agent becomes a gel; and flowing the liquid through the openings into contact with the sanitizing agent to cause at least some of the sanitizing agent to be mixed with the liquid; and leaching said at least some of the sanitizing agent through the flexible mesh fabric material wall for sanitizing the liquid flowing into the drain.

* * * * *